United States Patent [19]

Wu et al.

[11] Patent Number: 4,515,634

[45] Date of Patent: May 7, 1985

[54] CASTABLE GLASS-CERAMIC COMPOSITION USEFUL AS DENTAL RESTORATIVE

[75] Inventors: Jenn-Ming Wu, Tainan, Taiwan; Warren R. Cannon, East Brunswick; Carlino Panzera, Belle Mead, both of N.J.

[73] Assignee: Johnson & Johnson Dental Products Company, East Windsor, N.J.

[21] Appl. No.: 542,798

[22] Filed: Oct. 17, 1983

[51] Int. Cl.$^3$ .............................. C03C 3/22; C09K 3/00
[52] U.S. Cl. ........................................ 106/35; 65/33; 433/201; 433/202; 501/5; 501/63
[58] Field of Search ............................ 501/5, 6, 7, 63; 106/35; 433/201, 202; 65/33

[56] References Cited

U.S. PATENT DOCUMENTS

| | | |
|---|---|---|
| 3,282,712 | 11/1966 | Tashiro et al. .................... 501/63 |
| 3,809,543 | 5/1974 | Gaskell et al. ..................... 501/63 |
| 3,816,704 | 6/1974 | Borom et al. ...................... 501/5 |
| 3,977,857 | 8/1976 | Mattox .............................. 501/5 |
| 4,189,325 | 2/1980 | Barrett et al. .................... 501/63 |

FOREIGN PATENT DOCUMENTS 49-126712 12/1974 Japan ...................... 501/5

Primary Examiner—Helen M. McCarthy
Attorney, Agent, or Firm—Charles J. Metz

[57] ABSTRACT

A glass ceramic, useful in making dental crowns and bridges, consisting essentially of:

| Component | Broad Range, Mole Percent | Preferred Mole % |
|---|---|---|
| $Li_2O$ | 24–33 | 29.5 ± 1 |
| $SiO_2$ | 37–74.3 | 59.0 ± 3, −2 |
| $Al_2O_3$ | 0.5–4 | 1.5 ± 0.5 |
| CaO | 1–10 | 6.0 ± 1 |
| $P_2O_5$ | 0.2–4 | 2.0 + 0.5, −1 |
| TiO | 0–4 | 1.0 ± 0.5 |
| $ZrO_2$ | 0–4 | 1.0 ± 0.5 |
| MgO | 0–2 | — |
| $K_2O$ | 0–2 | — |

4 Claims, No Drawings

CASTABLE GLASS-CERAMIC COMPOSITION USEFUL AS DENTAL RESTORATIVE

The invention relates to a phosphorus-nucleated lithium silicate castable glass-ceramic composition having particular utility as a dental restorative.

BACKGROUND OF THE INVENTION

Glass-ceramics composed of lithium silicate glass have been proposed for use as dental restorative materials. For instance, see Barrett et al., U.S. Pat. No. 4,189,325 and reference cited therein. The patentees employ a mixture of elemental platinum and niobium oxide as nucleating agents to eliminate the problem of cracking caused by localized volume changes during crystallization. At col. 4, lines 55-59, the patentees state that "conventional nucleating agents such as $TiO_2$, $ZrO_2$ or $P_2O_5$ . . . " need not be used.

In accordance with this invention, we have found that if one employs $P_2O_5$ as a nucleating agent in lithium silicate glasses similar to those described by Barrett et al., in place of the patentees' $Pt-Nb_2O_5$ nucleating agents, a substantial and unexpected improvement in strength is obtained, along with the ability to attain concomitant high softening temperatures, which enhances the utility as a dental restorative material because the addition of a glaze to the dental restoration is thereby rendered less critical.

BRIEF SUMMARY OF THE INVENTION

The castable glass-ceramic composition provided by this invention has the following composition:

| COMPONENT | Broad Range, Mole % | Preferred Mole % |
|---|---|---|
| $Li_2O$ | 24-33 | 29.5 ± 1 |
| $SiO_2$ | 37-74.3 | 57-62 |
| $Al_2O_3$ | 0.5-4 | 1.5 ± 0.5 |
| $CaO$ | 1-10 | 6.0 ± 1 |
| $P_2O_5$ | 0.2-4 | 2.0 + 0.5, -1 |
| $TiO_2$ | 0-4 | 1.0 ± 0.5 |
| $ZrO_2$ | 0-4 | 1.0 ± 0.5 |
| $M_2O$ | 0-2 | — |
| $K_2O$ | 0-2 | — |

THE PRIOR ART

In addition to the Barrett et al. patent cited above, the following is considered to be the most relevant prior art:

Gaskell et al., in U.S. Pat. No. 3,804,608, and Borom et al., in U.S. Pat. No. 3,816,704, disclose certain lithium silicate glass-ceramic compositions containing $P_2O_5$ nucleating agents.

The following journal articles discuss various lithium silicate glass-ceramic compositions, and the use of various nucleating agents, including $P_2O_5$, therein: Harper et al., "The Formations of Glass-Ceramic Microstructures", Physics and Chemistry of Glasses, 13, No. 4, August 1972, pages 97-101.

Matusita et al., "Effect of Added Oxides on the Crystallization and Phase Separation of $Li_2O$, 3 $SiO_2$ Glasses", Physics and Chemistry of Glasses, 15, No. 4, August 1974, pages 106-108.

Hing et al. "The Strength and Fracture Properties of Glass-Ceramics", Journal of Materials Science 8 (1973) 1041-1048.

Borom et al., "Strength and Microstructure in Lithium Disilicate Glasses, J.Am.Cer. Soc. 58, No. 9-10, pages 385-391 (Sept.-Oct., 1975).

Doremus et al., "Crystallization of Lithium Disilicate in Lithium Silica Glasses", Physics and Chemistry of Glasses, Vol. 13, No. 1, Feb. 1972, pages 14 et seq.

DETAILED DESCRIPTION OF THE INVENTION

The castable glass-ceramic composition of the invention contains oxides of lithium, silicon, aluminum, calcium, and phosphorus, and, preferably, titanium and zirconium. Each of the compositions contributes to one or more desirable properties. For instance, lithium oxide is an excellent flux which enhances the fluidity and castability of the glass. The proportion of lithium and silicon is preferably chosen so as to approach as closely as possible the composition lithium disilicate, since glass-ceramics having lithium disilicate crystalline phases have very high strength.

Alumina is added to the glass to enhance chemical durability. Calcium oxide is added to compensate for the viscosity increase in the molten glass that results from the addition of alumina. At the same time, calcium oxide enhances the chemical durability of the glass-ceramic composition.

The phosphorus oxide is employed as a nucleating agent. Surprisingly, the use of $P_2O_5$ as the nucleating agent caused an unexpected strength increase, compared with similar glasses that use different nucleating agents.

The glass can be produced by blending, in the desired proportions, the oxides and/or compounds that decompose to form the oxides, followed by fusing the ingredients. Convenient raw materials include lithium carbonate, silica, alumina, calcium carbonate, titanium dioxide, zirconium dioxide, ammonium phosphate, and tricalcium phosphate. After blending, the mixed ingredients are fired to a temperature high enough to effect fusion (e.g., from about 1400° to 1450° C.) The melting time will usually be about 20 to 30 minutes, after which the melt is quenched by pouring into water. The quenched glass chunks are dried and then ground to a very fine powder, as by ball milling for several hours (e.g., 2 to 4 hours) to improve the homogeneity of the composition, and then remelted at about 1400°-1450° C. for 3 to 5 hours until a homogenous and bubble-free melt is produced. This melt may then be cast by standard procedures, such as spin casting, into the desired dental restoration, and the casting is then subjected to heat treatment to nucleate and grow crystallites within the glass. Different heat treatment temperatures can be used to optimize various properties, such as strength and softening temperatures, as is illustrated below in the examples.

In the Examples and Control Examples below, the following general Expermental procedure was used:

PREPARATION OF THE GLASS

The raw materials used in the preparation of glasses were reagent grade: $Li_2CO_3$, $SiO_2$, $Al_2O_3$, $CaCO_3$, $TiO_2$, $ZrO_2$, $H_3BO_3$, $PtCl_4-2HCl.6H_2O$ (all Fisher brand), $Ca_3(PO_4)_2$, $Nb_2O_5$ (Baker) and $ZnO$, $K_2CO_3$, $MgCO_3$ (Mallincrodt).

After weighing the raw materials, the batches were put in a glass jar and tumble-mixed for about a half hour. The mixed batches were put in a 500 milliliter $SiO_2$ crucible (Ferro) and melted in a gas furnace. The crucible was covered with a refractory plate during melting to reduce contamination and voltilization of the batches. The melting temperature was 1400°-1450° C., measured by optical pyrometer, and melting time was about 20-30 minutes. After melting, the melt was poured into water. The quenched glass chunks were dried in an oven overnight, and then put in a ball mill for 2 hours. The ground powder was then put in a platinum crucible and melted in an electric furnace at 1400° C. for 4 hours. The homogeneous and bubble free melt was poured into a copper mold, and transferred immediately to an annealing furnace preset at 450° C. for 1 hour. After annealing, the glass slab was furnace cooled to room temperature.

The glass slab was cut to the desired shape and heat treated in an electric furnace for various periods of time intended to nucleate and grow the crystallites within the glass.

Glasses were made from the foregoing reagents which had the compositions set forth in Table I (on a mole percent basis—weight percents are given in parentheses):

TABLE I

| Component | Example 1 | Control 1 | Control 2 | Control 3 | Control 4 | Control 5 |
|---|---|---|---|---|---|---|
| $Li_2O$ | 29.5 (16.4) | 30.5 (17.3) | 26.5 (14.9) | 25 (13.5) | 30 (17.3) | 27 (14.8) |
| $SiO_2$ | 59.0 (65.5) | 61.0 (69.3) | 67.1 (75.3) | 67 (72.6) | 68 (78.4) | 68 (74.7) |
| $Al_2O_3$ | 1.5 (2.8) | 2.5 (4.8) | 1.4 (2.7) | 1.5 (2.8) | — | — |
| CaO | 6.0 (6.2) | 6.0 (6.4) | — | — | — | 2 (2.1) |
| $P_2O_5$ | 2.0 (5.3) | — | 1.0 (2.7) | 2.5 (6.4) | 1 (2.7) | 2 (5.2) |
| $TiO_2$ | 1.0 (1.5) | — | — | — | — | — |
| $ZrO_2$ | 1.0 (2.3) | — | — | — | — | — |
| Pt | — | 0.0033 (0.012) | — | — | — | — |
| $Nb_2O_3$ | — | 0.5 (2.2) | — | — | — | — |
| $B_2O_3$ | — | — | 2.6 (3.4) | 1.5 (1.9) | — | — |
| $K_2O$ | — | — | — | 1.0 (1.7) | — | 1 (1.7) |
| ZnO | — | — | — | — | 1 (1.6) | 1 (1.5) |
| MgO | — | — | 1.4 (1.0) | 1.5 (1.1) | — | — |

For identification purposes, the controls illustrate the following glasses:

Control 1—Barrett et al., U.S. Pat. No. 4,189,325

Control 2—Borom et al., J.Am.Ceram.Soc., 58, No. 910, pages 385-391 (1975)

Control 3—Similar to Control 2, but with potassium added to soften the glass slightly and reduce the stress in the newly formed glass.

Control 4—Hing et al., J.Mat.Sci., 8, pages 1041-104 (1973)

Control 5—Similar to Control 4 but with calcium (for durability) and potassium (for stress release) added and phosphorus increased for more nucleation.

Dilatometer analysis was used to determine the softening temperature of each glass. The optimum nucleation temperature is about 15° to 30° C. higher than the softening temperature; therefore, the softening temperature is used to help determine the heat treatment schedule. The dilatometer softening temperatures were as follows:

TABLE II

| Sample | Softening Temperatures Temperature, °C. |
|---|---|
| Example 1 | 500 |
| Control 1 | 495 |
| Control 2 | 500 |
| Control 3 | 485 |
| Control 4 | 475 |
| Control 5 | cracked during |

TABLE II-continued

| Sample | Softening Temperatures Temperature, °C. |
|---|---|
| | cooling |

Based upon this information, the several glasses were heat treated to cause crystallization and crystal growth, and thereby form glass ceramics. The heat treatment schedules and the softening points of the resulting glass ceramics are presented in Table III. After the indicated heat treatment schedules, the power was shut off to the furnace and the furnace was allowed to cool.

TABLE III

Heat Treatment and Softening Temperatures of Glass Ceramics

| Sample | Heat Treatment | Softening Temp. |
|---|---|---|
| Example 1-a | 520° C. 4 hours 625° C. 20 hours | 750° C. |
| Example 1-b | 520° C. 4 hours 635° C. 20 hours | 825° C. |
| Control 1-a | 780° C. ½ hour 520° C. 4 hours, 620° C. 1 hour | 650° C. |
| Control 1-b | 520° C. 4 hours, 620° C. 24 hours | 665° C. |
| Control 1-c | 520° C. 4 hours, 620° C. 5 hours | 700° C. |
| Control 1-d | 520° C. 4 hours, 620° C. 5 hours 650° C. 4 hours, and slowly heated to 750° C. and soak for 1 hour | 925° C. |
| Control 2 | 520° C. 4 hours, 580° C. 4 hours 700° C. 5 hours | 750° C. |
| Control 3 | 500° C. 2.5 hours, 550° C. 2.5 hours, 740° C. 14 hours | 765° C. |
| Control 4 | 500° C. 1 hour, 550° C. 1 hour | 940° C. |
| Control 5 | 500° C. 2 hours, 545° C. 21 hours | 605° C. |

Castability properties of all of the glasses studied were found to be acceptable, although the Example 1 glass was slightly more castable than Controls 1, 2, and 3.

The samples of Controls 4 and 5 cracked during the cooling period after heat treatment, thereby indicating inadequate thermal shock resistance.

The flexural strengths of the Example 1 and Control 1 glass ceramics were determined as a function of heat treatment schedules. The procedure for determining the flexural strengths was the standard 3-point bending test with unground samples. (The procedure was a modified ASTM C-674 procedure using a one inch span on specimens 3/10 inch wide and 0.15 inch thick.).

The results of the flexural strength determinations are displayed in Tables IV and V:

TABLE IV

| Heat Treatment | Example 1 Softening Temperature | Flexural Strength |
|---|---|---|
| (a) 510° C. 4 hours<br>625° C. 20 hours | | Average = 48,296 psi<br>Standard<br>Deviation = 6,220 psi |
| (b) 520° C. 4 hours<br>625° C. 20 hours | 750° C. | Average = 44,337 psi<br>Standard<br>Deviation = 5,375 psi |
| (c) 525° C. 4 hours<br>625° C. 20 hours | | Average = 43,534 psi<br>Standard<br>Deviation = 8,775 psi |
| (d) 510° C. 4 hours<br>625° C. 20 hours<br>780° C. ½ hour | 825° C. | Average = 43,199 psi<br>Standard<br>Deviation = 4,907 psi |
| (e) 510° C. 13 hours<br>625° C. 27.5 hours | | Average = 43,199 psi<br>Standard<br>Deviation = 2,431 psi |

TABLE V

| Heat Treatment | Control 1 Softening Temperature | Strength |
|---|---|---|
| (a) 520° C. 4 hours<br>620° C. 4 hours<br>slowly to 750 C. | 925° C. | 20,000 psi |
| (b) 520° C. 4 hours<br>620° C. 24 hours | 665° C. | 34,000 psi |
| (c) 500° C. 1 hour<br>550° C. 24 hours | | 22,000 psi |
| (d) 520° C. 4 hours<br>620° C. 20 hours | | 28,900 psi |

As the Examples above illustrate, the subject glass ceramic has an excellent combination of properties. It has low viscosity at 1300° C., and therefore can be readily cast; when crystallized, it has high strength (between about 40,000 and 52,000 psi, depending on the heat treatment); and it has a high softening point (750° to 825° C.) so that a porcelain glaze can be applied to it. It has also been found to have good chemical stability, as has been determined in accelerated aging tests by exposure to 4 percent aqueous acetic acid. (This is illustrated in Example 2 below.) The thermal shock behavior of the glass ceramic of the invention is also acceptable. It can be introduced into an 800° C. oven and removed many times without degradation.

EXAMPLE 2 AND CONTROL 6

A glass-ceramic of the same composition of Example 1 was heat treated at 510° C. for 4 hours, 625° C. for 20 hours, and 780° C. for ½ hour, and then tested for chemical durability. It was compared to a commercial dental porcelain (Control 6).

Initially, leaching tests were performed under carefully controlled conditions. The leaching solution was 4% acetic acid held at 25° C., with surface area/volume ratio (i.e., surface area of sample per volume of leaching solution)=0.01. The results are summarized in Table VI.

It is found that Example 2 glass-ceramic has a higher lithium leaching, but lower sodium and potassium leaching than Control 6. The commercial dental porcelain had a lower total alkali leaching rate. The Example 2 glass-ceramic was of the same order of magnitude.

Our conclusion is that the Example 2 glass-ceramic can be thought as having excellent chemical durability.

TABLE VI

Summary of Leaching Test in 4% Acetic Acid at 25° C. for SA/V = 0.01

| Sample | Leaching Time Days | Li (ppm) | Na (ppm) | K (ppm) | Total Alkali (ppm) |
|---|---|---|---|---|---|
| Example 2 | | | | | |
| 510° C. 4 hrs. | 2 | 0.23 | 0.016 | 0 | 0.246 |
| 625° C. 20 hrs. | 3 | 0.27 | 0.024 | 0 | 0.294 |
| 780° C. 0.5 hrs. | 4 | 0.32 | 0.030 | 0 | 0.350 |
| Commercial | | | | | |
| Dental Porcelain | 2 | 0 | 0.052 | 0.018 | 0.070 |
| (Control 6) | 3 | 0 | 0.052 | 0.020 | 0.072 |
| | 4 | 0 | 0.052 | 0.018 | 0.070 |

The sodium ions were trace impurities in the glass-ceramic of Example 2.

What is claimed is:

1. A glass-ceramic having high strength and a high softening temperature, consisting essentially of the following constituents, on a mole percent basis:

| $Li_2O$ | 28.5–30.5 |
|---|---|
| $SiO_2$ | 57–62 |
| $Al_2O_3$ | 1–2 |
| CaO | 5–7 |
| $P_2O_5$ | 1–2.5 |
| $TiO_2$ | 0.5–1.5 |
| $ZrO_2$ | 0.5–1.5 | wherein the crystalline phase is lithium disilicate, said glass ceramic having a flexural strength of from about 40,000 psi to about 52,000 psi, and a softening temperature of from about 750° C. to about 825° C.

2. A dental restoration comprising the glass-ceramic of claim 1.

3. The glass-ceramic of claim 1 having the following composition, on a mole percent basis:

| $Li_2O$ | 29.5 |
|---|---|
| $SiO_2$ | 59.0 |
| $Al_2O_3$ | 1.5 |
| CaO | 6.0 |
| $P_2O_5$ | 2.0 |
| $TiO_2$ | 1.0 |
| $ZrO_2$ | 1.0 |

4. A dental restoration comprising the glass-ceramic of claim 3.

* * * * *